(12) United States Patent
Anai et al.

(10) Patent No.: US 7,326,547 B2
(45) Date of Patent: Feb. 5, 2008

(54) SOYBEAN MUTANT STRAIN AND SOYBEAN OIL THEREFROM

(75) Inventors: Toyoaki Anai, Saga (JP); Yutaka Takagi, Saga (JP)

(73) Assignee: Saga Prefectural Regional Industry Support Center, Saga (JP)

( * ) Notice: Subject to any disclaimer, the term of this patent is extended or adjusted under 35 U.S.C. 154(b) by 707 days.

(21) Appl. No.: 10/419,865

(22) Filed: Apr. 22, 2003

(65) Prior Publication Data

US 2004/0103450 A1     May 27, 2004

(30) Foreign Application Priority Data

Apr. 22, 2002   (JP)  ............... 2002-119821

(51) Int. Cl.
*C12P 19/34*     (2006.01)
*C07H 21/04*     (2006.01)

(52) U.S. Cl. .................. 435/91.2; 536/23.1; 435/6

(58) Field of Classification Search ............ None
See application file for complete search history.

(56) References Cited

U.S. PATENT DOCUMENTS

2004/0006792 A1*   1/2004   Fillatti et al. ............... 800/281

OTHER PUBLICATIONS

N. Yadav et al., "Cloning of Higher Plant ω-3 Fatty Acid Desaturases", Plant Physiol. vol. 103, pp. 467-476, 1993.
J. R. Byrum et al., "Alteration of the Omega-3 Fatty Acid Desaturase Gene is Associated with Reduced Linolenic Acid in the A5 Soybean Genotype", Theor. Appl. Genet, vol. 94, pp. 356-359, 1997.

* cited by examiner

*Primary Examiner*—Phuong Bui
*Assistant Examiner*—Brendan O. Baggot
(74) *Attorney, Agent, or Firm*—Wenderoth, Lind & Ponack, L.L.P.

(57) ABSTRACT

A soybean oil of a decreased content of polyunsaturated fatty acids is produced by hybridizing, selecting and raising a soybean mutant KK21 characterized by a gene having a sequence of base given by the sequence No. 1 of the sequence listing, a soybean mutant M23 characterized by deletion of a gene having a sequence of base given by the sequence No. 2 of the sequence listing, a soybean mutant M24 characterized by a gene having a sequence of base given by the sequence No. 3 of the sequence listing, a soybean mutant M5 characterized by a gene having a sequence of base given by the sequence No. 4 of the sequence listing, a soybean mutant J18 characterized by deletion of a gene having a sequence of base given by the sequence No. 5 of the sequence listing, and one or two kinds or more of these soybean mutants.

1 Claim, 6 Drawing Sheets

Bay(control) Gm FAD 2-1

KK21 Gm FAD 2-1

Bay(control) FAD3-1b

M5 FAD3-1b

SOYBEAN MUTANT STRAIN AND SOYBEAN OIL THEREFROM

BACKGROUND OF THE INVENTION

The present invention relates to a novel mutant strain obtained by irradiation with X-rays using a soybean strain Bay as a new strain, and a soybean oil of a decreased content of polyunsaturated fatty acids obtained therefrom.

In general, a triacylglycerol which is a main component of fats and oils present in plants, particularly their seeds, is a compound obtained by bonding three fatty acid molecules to one glycerol molecule, and depending on the kind of the bonded fatty acid, physical and chemical properties and nutritive values are different. The composition of the fatty acids is specific to plant species from which they are derived, and therefore, it is impossible to avoid limitation of its use for each plant species.

On the other hand, for suppressing degeneration by oxidation in storage of this plant fat and oil, it is necessary to decrease the content of polyunsaturated fatty acids liable to be oxidized.

It is known that, in a soybean seed, a biosynthesis system of palmitic acid →stearic acid →oleic acid →linolic acid → linolenic acid is present, and conversion from oleic acid into linolic acid is conducted with a microsomal ω-6 fatty acid desaturase enzyme and conversion from linolic acid into linolenic acid is conducted with a microsomal ω-3 fatty acid desaturase enzyme, and that ω-6 and ω-3 fatty acid desaturations with these enzymes are correlated with a plurality of genes, and known that parts of them are controlled by genes at the FAD 2-position and FAD 3-position [Plant Physiol., (1993), vol. 103, pages 467-476 and Theor. Appl. Genet., (1997), vol. 94, pages 356-359].

SUMMARY OF THE INVENTION

The present invention has been accomplished intending a mutant usable in strain-improvement to decrease the content of polyunsaturated fatty acids in a soybean seed and production of a soybean oil of a decreased content of polyunsaturated fatty acids using the above-mentioned mutant as a raw material.

The present inventors have intensively studied for obtaining a soybean strain which gives a soybean oil of improved quality, and resultantly found that a mutant obtained by irradiation with X-rays using a soybean strain Bay as a new strain allows production of an oil of a decreased content of linolic acid and linolenic acid, leading to completion of the invention based on this finding.

Namely, the present invention provides a method of producing a soybean oil of a decreased content of polyunsaturated fatty acids comprising: hybridizing, selecting and raising a soybean mutant KK21 characterized by a gene having a sequence of base given by the sequence No. 1 of the sequence listing, a soybean mutant M23 characterized by deletion of a gene having a sequence of base given by the sequence No. 2 of the sequence listing, a soybean mutant M24 characterized by a gene having a sequence of base given by the sequence No. 3 of the sequence listing, a soybean mutant M5 characterized by a gene having a sequence of base given by the sequence No. 4 of the sequence listing, a soybean mutant J18 characterized by deletion of a gene having a sequence of base given by the sequence No. 5 of the sequence listing, and one or two kinds or more of these soybean mutants.

DETAILED DESCRIPTION OF PREFERRED EMBODIMENTS

Figure 1:
FIG. 1 is a view showing the analysis pattern of a gene of a soybean mutant KK21.
Figure 1:
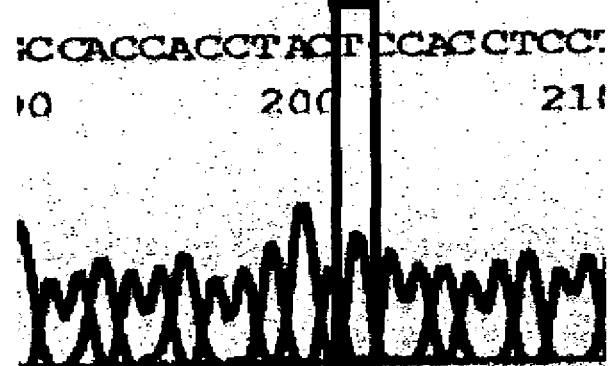

The mutant gene of the present invention having a sequence of base given by the sequence No. 1 of the sequence listing characterizing a soybean mutant KK21 is obtained by deletion of thymine (t), the 233rd base from the initiation codon, in FAD2-1 which is one of microsomal ω-6 fatty acid desaturase enzyme genes in soybean, and because of this reason, one of enzymes necessary for synthesis of linolic acid is not formed normally. As the feature of a soybean mutant M23, expression of a FAD2-1 gene having a sequence of base given by the sequence No. 2 of the sequence listing is not found, and one of necessary enzymes is not synthesized. The mutant gene having a sequence of base given by the sequence No. 3 of the sequence listing characterizing a soybean mutant M24 is obtained by deletion of adenine (a), 1078th base from the initiation codon, in FAD3-1a which is one of microsomal ω-3 fatty acid desaturase enzyme genes in soybean, and because of this reason, one of enzymes necessary for synthesis of linolenic acid is not formed normally. The mutant gene having a sequence of base given by the sequence No. 4 of the sequence listing characterizing a soybean mutant M5 is obtained by deletion of bases from the 1033rd base, cytosine (c), to the 1051st base, guanine (g) from the initiation codon in FAD3-1b, and because of this reason, one of enzymes necessary for synthesis of linolenic acid is not formed normally. Further, as the feature of a soybean mutant J18, expression of a FAD3-1b gene having a sequence of base given by the sequence No. 5 of the sequence listing is not found, and one of necessary enzymes is not synthesized.

These soybean mutants are obtained by irradiating 4000 parent soybean strain Bays with X-rays at an intensity of 1 Sv/minute for 200 minutes at a total dosage of about 200 Sv (sievert) to induce mutation.

Then, seeds thus irradiated with X-rays, namely, irradiated first generation seeds (hereinafter, referred to as M1 seed) are disseminated on the field and cultivated to obtain self-propagating progeny, namely, irradiated second generation seeds (hereinafter, referred to as M2 seed). Then, irradiated third generation seeds (hereinafter, referred to as M3 seed) are raised from the irradiated M2 seeds in the same manner, and the composition of fatty acid is analyzed for each individual of M2 seeds. Thus, from the analysis results of the fatty acid compositions, it was confirmed that on average 4 to 5 mutants are generated from about 2000 M2 seeds, and mutants were separated. Regarding irradiated M4 generation and followings obtained from the thus obtained M3 seeds, experiments confirming mutants were conducted sequentially to obtain respective mutants.

In the present invention, detection of these respective genes can be conducted by a RT-PCR (reverse transcribed-polymerase chain reaction) method, a combination of this method with a dideoxy method, or a Southern blotting method, as shown in the following methods (1) to (5).

(1) Detection of variant FAD2-1 gene generated in KK21 line (high oleic acid mutant line):

This can be conducted, by combining a RT-PCR method with a dideoxy method, as follows. Namely, all RNAs are extracted from a plant material (immature seed) according to an ordinary method, then, a cDNA is produced using an oligo-dT primer according to an ordinary method. Next, using this cDNA as a template, a PCR reaction is conducted according to an ordinary method using a primer 1: 5'-attgat-agcccctccgttcccaaga-3' (SEQ ID NO: 6) and a primer 2: 5'-attgtgagtgtgacgagaagagaaac-3' (SEQ ID NO: 7) to amplify a part of a sequence of base of a FAD2-1 gene, then, using the purified DNA as a template, the analysis of a sequence of base is conducted according to an ordinary method using a primer 3: 5'-gggtctagcaaaggaaacaacaatgg-gaggt-3 (SEQ ID NO: 8). As a result, identification of a variant FAD2-1 gene derived from the KK21 line is possible if deletion of a base t shown in FIG. 1 is observed.

Figure 2:
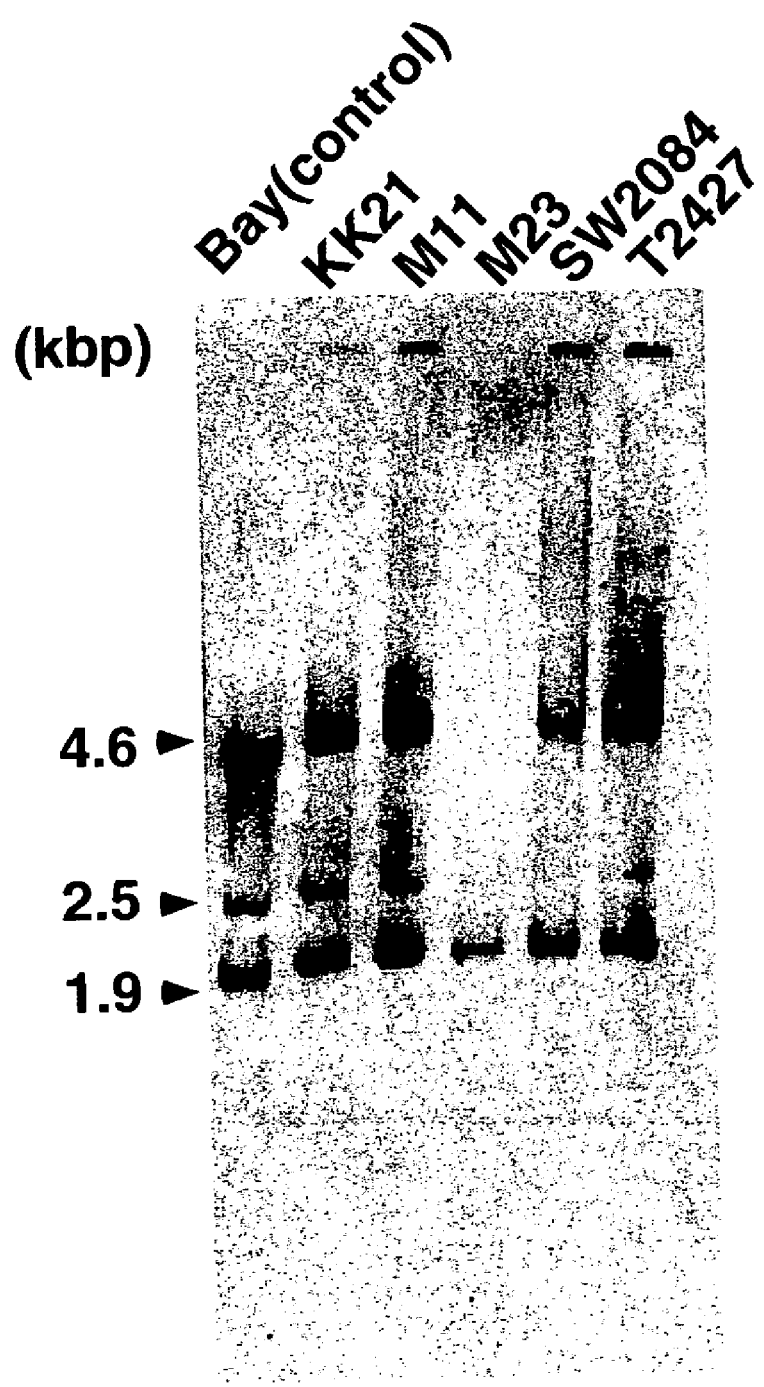
FIG. 2 is a view showing the analysis pattern of a gene of a soybean mutant M23 and other genes compared with it according to a Southern blotting method.

(2) Detection of variant FAD2-1 gene generated in M23 line (high oleic acid mutant line):

(a) Detection by Southern blotting method; DNA obtained by extraction according to an ordinary method from a plant material (any tissue of leaf, seed, root and the like is possible) is digested using a restriction enzyme EcoR I, and analyzed by a Southern blotting method according to an ordinary method. In this operation, a FAD2-1 gene is used as a probe, however, labeling of a probe may be conduced by any of methods using a radioactive isotope or methods using chemical modifications, without causing problems. In a Bay (parent strain) having a normal FAD2-1 gene, three bands of about 1.9 kbp, 2.5 kbp and 4.6 kbp are detected, and when a variant FAD2-1 gene derived from M23 line is present, this can be identified by disappearance of a band of about 4.6 kbp. Analysis pattern by this method is shown in FIG. 2.

Figure 3:
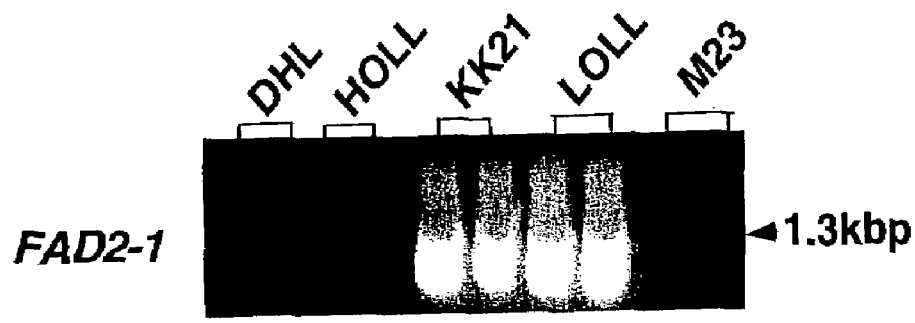
FIG. 3 is a view showing the analysis pattern of a gene of a soybean mutant M23 and other genes compared with it according to a RT-PCR method.

(b) Detection by RT-PCR method; All RNAs are extracted from a plant material (immature seed) according to an ordinary method, then, a eDNA is produced using an oligo-dT primer according to an ordinary method. Next, using this cDNA as a template, a PCR reaction is conducted according to an ordinary method using a primer 1: 5'-attgatagcccctc-cgttcccaaga-3' (SEQ ID NO: 6) and a primer 4: 5'-atacaca-caaagtcattacgcggcaa-3'(SEQ ID NO: 9) to amplify a sequence of base including the overall length of a protein coding region of a FAD2- 1 gene. When this reaction product is analyzed by an agarose electrophoresis method according to an ordinary method, one band of about 1.3 kbp is detected in a Bay (parent strain) having a normal FAD2-1 gene, while in the case of a variant FAD2-1 gene derived from M23 line, this can be identified by utterly no detection of bands. The analysis data by this method are shown in FIG. 3.

Figure 4:
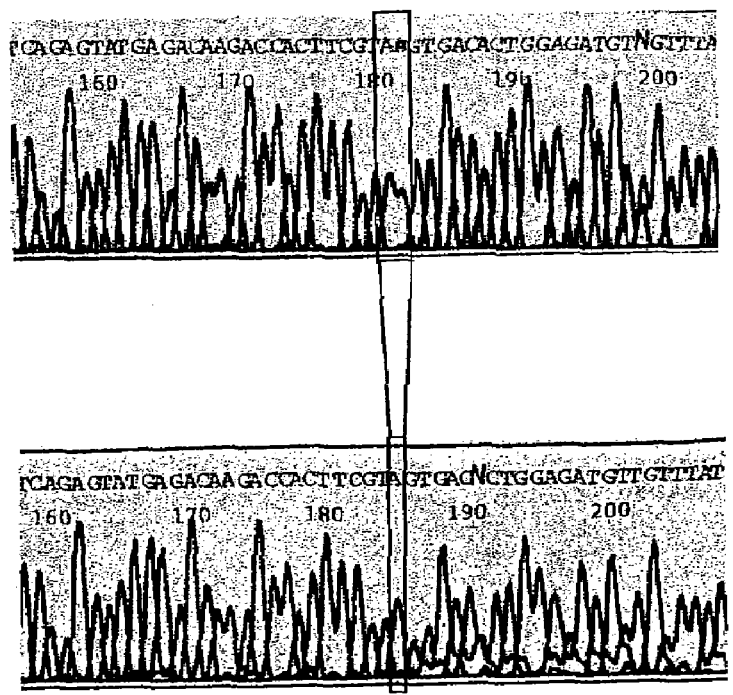
FIG. 4 is a view showing the analysis pattern of a gene of a soybean mutant M24.

(3) Detection of variant FAD3-1a gene generated in M24 line (low linolenic acid mutant line):

This can be conducted, by combining a RT-PCR method with a dideoxy method, as follows. All RNAs are extracted from a plant material (immature seed) according to an ordinary method, then, a cDNA is produced using an oligo-dT primer according to an ordinary method. Next, using this cDNA as a template, a PCR reaction is conducted according to an ordinary method using a primer 5: 5'-ttattacgcaccac-ccaccaccgtatccct-3' (SEQ ID NO: 10) and a primer 6: 5'-gttgcgagtggaggagcagagaatcagtc-3' (SEQ ID NO: 11) to amplify sequences of base containing the overall lengths of protein coding regions of FAD3-1a and FAD3-1b genes simultaneously. Then, DNA fragments purified according to an ordinary method are digested using a restriction enzyme Kpn I, and only a FAD3-1a is separated from a DNA fragment of about 1.2 kbp and purified using agarose gel, then, using this as a template, the analysis of a sequence of base is conducted according to an ordinary method using a primer 7: 5'-gtggatcgtgactatggttggatcta-3' (SEQ ID NO: 12). The analysis pattern in this operation is shown in FIG. 4. As a result, identification of a variant FAD3-1a gene derived from the M24 line is possible if deletion of a base as shown in FIG. 4 is observed.

Figure 5:
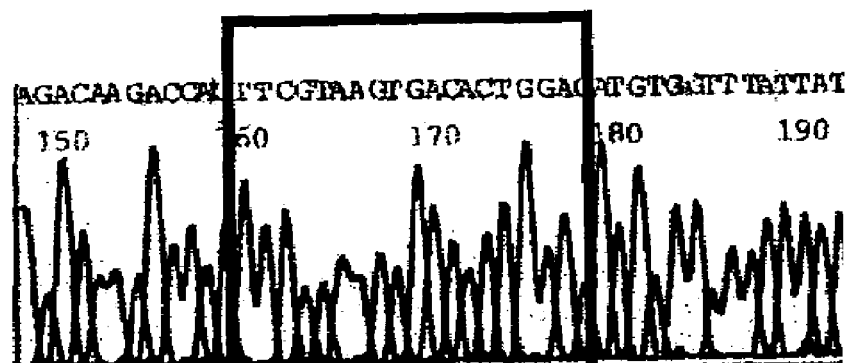
FIG. 5 is a view showing the analysis pattern of a gene of a soybean mutant M5.
Figure 5:
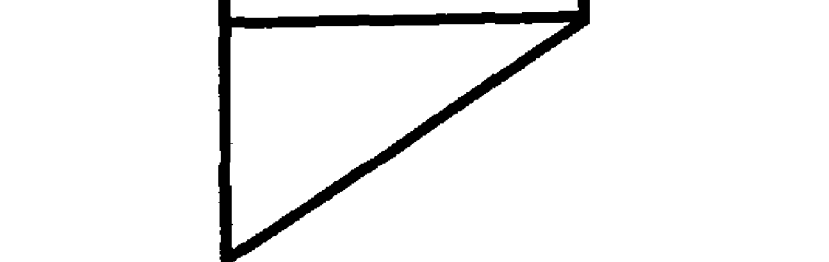

(4) Detection of variant FAD3-1b gene generated in M5 line (low linolenic acid mutant line):

This can be conducted, by combining a RT-PCR method with a dideoxy method, as follows. All RNAs are extracted from a plant material (immature seed) according to an ordinary method, then, a cDNA is produced using an oligo-dT primer according to an ordinary method. Next, using this cDNA as a template, a PCR reaction is conducted according to an ordinary method using a primer 5: 5'-ttattacgcaccac-ccaccacgtatccct-3' (SEQ ID NO: 10) and a primer 6: 5'-gt-tgcgagtggaggagcagagaatcagtc-3' (SEQ ID NO: 11) to amplify sequences of base containing the overall lengths of protein coding regions of FAD3-1a and FAD3-1b genes simultaneously. Then, DNA fragments purified according to an ordinary method are digested using a restriction enzyme Kpn I, and a DNA fragment of about 0.3 kbp only of a FAD3-1b gene is separated and purified using agarose gel, then, using this as a template, the analysis of a sequence of base is conducted according to an ordinary method using a primer 7: 5'-gtggatcgtgactatggttggatcta-3' (SEQ ID NO: 12). The analysis pattern in this operation is shown in FIG. 5. As a result, identification of a variant FAD3-1b gene derived from the MS line is possible if deletion of 19 bases (5'-cttcgtaagtgacactgga-3') (SEQ ID NO: 13') shown in FIG. 5 is observed.

Figure 6:
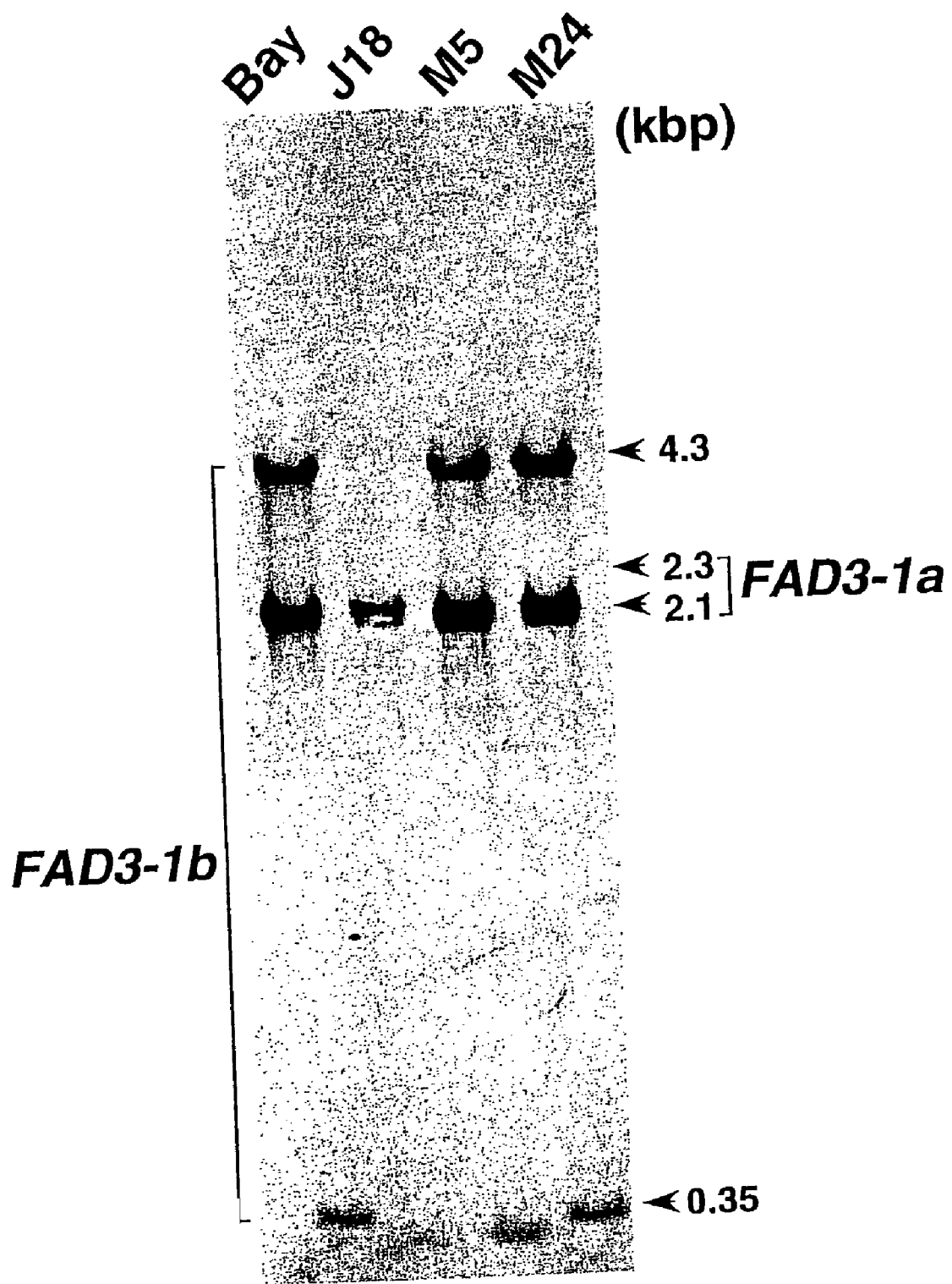
FIG. 6 is a view showing the analysis pattern of a gene of a soybean mutant J18 and other genes compared with it according to a Southern blotting method.

(5) Detection of variant FAD3-1b gene generated in J18 line (low linolenic acid mutant line):

(a) Detection by Southern blotting method; DNA obtained by extraction according to an ordinary method is digested using a restriction enzyme EcoR I, and analyzed by a Southern blotting method according to an ordinary method. In this operation, a FAD3-1b gene is used as a probe, however, labeling of a probe may be conduced by any of methods using a radioactive isotope or methods using chemical modifications, without causing problems. In a Bay (parent strain) having a normal FAD3-1b gene, four bands of about 0.35 kbp, 2.1 kbp, 2.3 kbp and 4.3 kbp are detected, and when a variant FAD3-1b gene derived from J18 line is present, this can be identified by disappearance of two bands of about 0.35 kbp and 4.3 kbp. Analysis pattern by this method is shown in FIG. 6.

Figure 7:
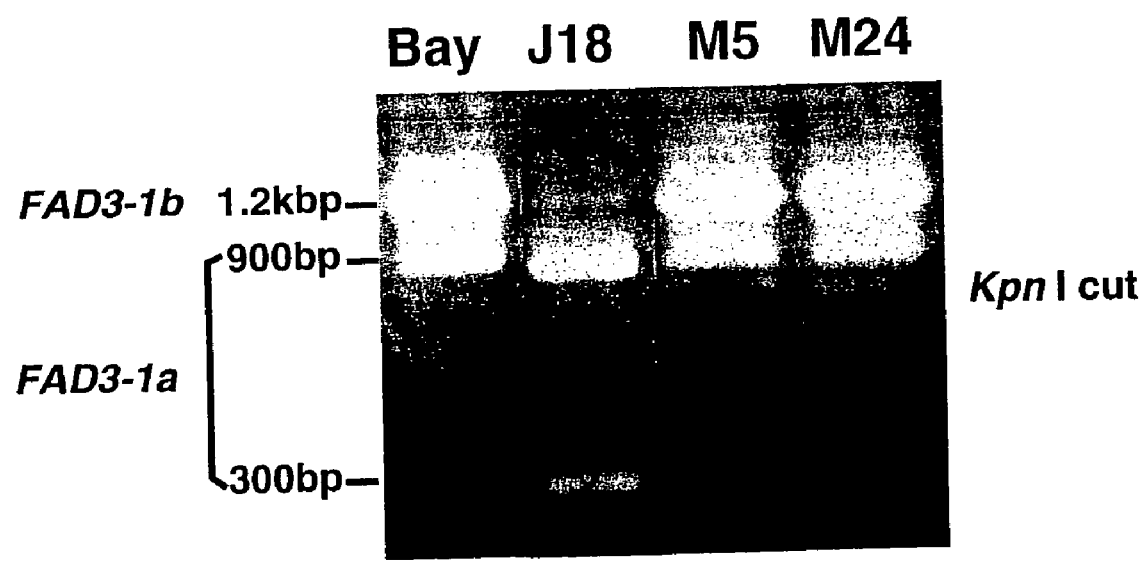
FIG. 7 is a view showing the analysis pattern of a gene of a soybean mutant J18 and other genes compared with it according to a RT-PCR method.

(b) Detection by RT-PCR method; All RNAs are extracted from a plant material (immature seed) according to an ordinary method, then, a cDNA is produced using an oligo-dT primer according to an ordinary method. Next, using this cDNA as a template, a PCR reaction is conducted according to an ordinary method using a primer 5: 5'-ttattacgcaccac-ccaccacgtatccct-3' (SEQ ID NO: 10) and a primer 6: 5'-gt-tgcgagtggaggagcagagaatcagtc-3' (SEQ ID NO: 11) to amplify sequences of base containing the overall lengths of protein coding regions of FAD3-1a and FAD3-1b genes simultaneously. DNA fragments purified according to an ordinary method are digested using a restriction enzyme Kpn I, and DNA fragments are separated using agarose gel. As a result, in Bays (parent strains) having normal FAD3-1a and FAD3-1b genes, a DNA fragment of about 1.2 kbp derived from a FAD3-1b gene and DNA fragments of about 900 bp and 300 bp derived from FADS-1a gene are detected, while in the case of a variant FAD3-1b gene derived from a J18 line, this can be identified by disappearance of a DNA fragment of about 1.2 kbp of them. Analysis data of this method are shown in FIG. 7.

Next, the present invention will be illustrated further in detail by examples, but the scope of the invention is not limited by these examples at all.

In the following examples, a parent Bay and, three mutants M24, M5 and J18 of low linolenic acid content obtained by irradiation on the Bay with X-rays, were cultivated in greenhouses of Saga University, Department of Agriculture, and leaves were sampled, then, frozen in liquid nitrogen and stored in a freezer of −80° C., before using as a plant material.

EXAMPLES

(1) Extraction of Genomic DNA

Frozen leaves were ground in a mortar, then, to 1 g of this powder was added 3 ml of 2% CTAB buffer [10 mM Tris-HCl (pH 8.0), 1.4 M NaCl, 20 mM EDTA, 2% CTAB], and the mixture was stirred gently. This was incubated on a water bath of 65° C. for 30 minutes and the same volume of chloroform was added and stirred gently, then, centrifugal separation was conducted at 4° C. under 8000 rpm for 10 minutes to remove proteins, and again, proteins in the aqueous layer were removed by extraction with chloroform. This aqueous layer was transferred to another centrifugal tube, and 1% CTAB precipitation buffer [50 mM Tris-HCl (pH 8.0), 1% CTAB] was added so that the total amount was 12 ml and they were mixed gently, then, centrifugal separation was conducted at 4° C. under 8000 rpm for 10 minutes to precipitate a CTAB-DNA complex. The supernatant was discarded, then, the precipitate was dissolved in 4 ml of 1M NaCl for removal of CTAB, and 4 ml of isopropanol was added, and centrifugal separation was conducted at 4° C. under 8000 rpm for 10 minutes to recover DNA. This precipitate was washed with 70% ethanol, then, dissolved in 200 µl of TE buffer [10 mM Tris-HCl (pH 8.0), 1 mM EDTA] containing RNase A (10 µg/µl), and incubated at 37° C. for 1 hour to digest RNA. For removal of proteins, to this was added the same volume of TLE saturated phenol-chloroform (1:1), and centrifugal separation was conducted at 4° C. under 15000 rpm for 5 minutes, the aqueous layer was moved to a new centrifugal tube of 1.5 ml and an extraction operation was conducted again, then, phenol in the aqueous layer was removed using only chloroform. These samples were subjected to electrophoresis together with λDNA not cut, the concentration was measured, then, the mixture was controlled so that the DNA concentration was 0.2 µg/µl and stored at −20° C.

(2) Preparation of Total RNA

According to a method obtained by improving a phenol/SDS method, soybean seeds sampled at four stages (5 mm or less, 5 to 7 mm, 7 to 10 mm and 10 mm or more) were frozen in liquid nitrogen, and ground in a mortar, then, to 5 g of this powder was added 25 ml of extraction buffer [180 mM Tris-HCl (pH 8.2), 90 mM LiCl, 4.5 mM EDTA, 1% SDS] and 10 ml of water-saturated phenol, and the mixture was stirred using a polytron type homogenizer at a maximum speed for about 1 minute. Further, 9 ml of chloroform was added and stirred sufficiently, and subjected to centrifugal separation at 4° C. under 8000 rpm for 10 minutes. This aqueous layer was moved to a new centrifugal tube, and to this was added 5 ml of 2 M NaOAc (pH 4.0) and each 5 ml of water-saturated phenol and chloroform and the mixture was stirred sufficiently, and subjected to centrifugal separation at 4° C. under 8000 rpm for 10 minutes. Thereafter, extraction with 10 ml of water-saturated phenol and chloroform was repeated six times in total, then, the supernatant was extracted with 10 ml of chloroform to remove phenol. 15 ml of 8 M LiCl was added to this aqueous layer, and the mixture was stirred gently up and down, then, allowed to stand still overnight on ice to precipitate a lithium salt of RNA, and subjected to centrifugal separation at 4° C. under 8000 rpm for 10 minutes to recover the precipitate. The thus obtained precipitate was dissolved in 500 µl of sterile water, moved to a 1.5 ml centrifugal tube, then, 3 M NaOAc of ¹⁄₁₀ amount was added and cooled on ice for 30 minutes, then, subjected to centrifugal separation at 4° C. under 15000 rpm for 5 minutes, to remove polysaccharides contaminated. 750 µl of isopropanol corresponding to 1.5-fold amount was poured into a 1.5 ml centrifugal tube and the supernatant was added into this tube, and subjected to centrifugal separation at 4° C. under 15000 rpm for 5 minutes, then, the supernatant was discarded and the precipitate was dissolved in 500 µl of sterile water.

(3) Purification of cDNA

A reaction solution of a total amount of 20 µl containing 50 mM Tris-HCl (pH 8.3), 75 mM KCl, 3 mM MgCl$_2$, 10 mM DDT, 300 µM dNTPs, 0.5 µg of Oligo-dT primer and 200 units of M-MLV reverse transcriptase (manufactured by GIBCO-BRL) was incubated for 1 hour at 37° C. to synthesize cDNA from 5 µg of total RNA. Next, using 1 µl of this 10-fold-diluted cDNA solution as a template, 20 µl of a PCR reaction solution was prepared containing 0.4 µl of Advantage II polymerase (manufactured by CRONTECH), 1×Advantage II buffer, 1×GC-RICH solution, 250 µM dNTPs and 0.1 pmol of a primer, and a PCR reaction was conducted. As conditions for the PCR reaction, one cycle of incubation at 95° C. for 2 minutes was conducted, subsequently, reaction cycle incubation at 95° C. for 30 seconds, at 65° C. for 30 seconds and at 72° C. for 3 minutes was repeated 35 times. The thus obtained PCR product was subjected to electrophoresis treatment at 100 V for 30 minutes using 1% agarose gel, and the intended cDNA fragment (Gm FAD3-1: about 1.2 kbp, Gm FAD3-2: about 1.3 kbp) detected by staining with ethidium bromide was recovered from the gel using QIAEX II Gel Extraction Kit (manufactured by QIAGEN).

(4) Production of RNA Probe

To 1 µl of a plasmid (pGEM-T Easy Vecter), 5 µl of T4 DNA Ligase, 1×Rapid Ligation buffer and 1 µl of T4 DNA Ligase was added 3 μl of purified FAD3-1 or FAD3-2 gene fragment, and the mixture was incubated at 12° C. overnight. The ligated plasmid was transformed into *E. coli* (XL-10 Gold), then, plated on a LB agar medium containing 50 mg/l of carbenicillin, 40 mg/l of X-gal and 200 μM of IPTG, and cultured overnight at 37° C., then, white colonies were selected, and incorporation and direction of fragments were confirmed using a PCR method. Bacteria holding the intended plasmid were inoculated on a LB liquid medium containing carbenicillin and cultured at 37° C. for about 14 hours, then, the plasmid was extracted. A PCR reaction was conducted using the thus obtained plasmid as a template to amplify DNA fragments containing a multi-cloning site, and purified by agarose electrophoresis. This DNA fragment was subjected to a protease treatment [0.5% SDS, 20 μm/ml protease] at 37° C. for 2 hours to completely digest RNase mixed in the DNA solution, and the protease was removed by extraction twice with phenol-chloroform. To this supernatant was added 75 μl of isopropanol and 5 μl of 3 M NaOAc and the mixture was cooled at −80° C. for 15 minutes, then, subjected to centrifugal separation at 4° C. under 15000 rpm for 10 minutes, and the thus obtained precipitate was dissolved in 20 μl of sterile water. A RNA probe labeled with DIG RNA Labeling Mix (manufactured by Roche) was produced using this DNA as a template.

(5) Southern Blotting Analysis

Genomic DNA was completely digested by EcoR I, and separated depending on the molecular weight by 1% agarose gel electrophoresis. A DNA fragment on this gel was transferred with an alkali solution [1.5 M NaCl, 0.5 M NaOH], and transferred to Biodyne plus membrane (manufactured by PALL). Thereafter, pre-hybridization was conducted at 50° C. for 5 hours or more in high SDS concentration hybridization buffer [50% formamide, 5×SSC, 0.1% N-lauroylsarcosine, 0.02% SDS, 1% blocking reagent], and RNA probes for DIG-labeled Gm FAD3-1 and Gm FAD3-2 were added, further, hybridization was conducted overnight at 50° C. Then, the membrane was washed twice in an aqueous solution containing 2×SSC and 0.1% SDS each for 5 minutes, further, washed three times in an aqueous solution containing 0.1×SSC and 0.1% SDS at 65° C. each for 20 minutes, to remove excess probes adhered to the membrane, then, washed with washing buffer [0.1 M maleic acid, 0.15 M NaCl, 0.3% Tween 20 (pH 7.5)] of room temperature for removal of SDS for 5 minutes. Then, a blocking reaction was conducted for 1 hour in buffer 2 [0.1 M maleic acid, 0.15 M NaCl, 0% blocking reagent (pH 7.5)], and incubation was conducted for 1 hour in the buffer 2 containing 1000-fold-diluted Anti-Digoxigenin-APFAB fragments (manufactured by Roche), to bond a label antibody to the DIG-labeled probe. Thereafter, washing in washing buffer was conducted three times each for 15 minutes, to remove excess antibodies. This was equilibrated in buffer 3 [10 mM Tris-HCl, 10 mM NaCl, 1 mM $MgCl_2$], then, incubation was conducted for 5 minutes in a CDP-Star solution (manufactured by Roche), and the membrane was sealed with a wrapping and incubated at 37° C. for 15 minutes. Chemoluminescence was detected by allowing it to be sensitized on an X-ray film.

(6) Northern Blotting Analysis

5 μg of total RNA was separated by electrophoresis using 1.2% formaldehyde agarose gel [1×MOPS buffer, 5% formaldehyde, 1.2% agarose], and transferred onto Biodyne plus membrane (manufactured by PALL) by using 20×SSC buffer. The membrane was rinsed with 2×SSC, then, irradiated with UV light of 70 $mJ/cm^2$ using UV cross-linker (manufactured by Amersham Pharmacia) to fix RNA. Hybridization was conducted at 65° C. using high SDS concentration hybridization buffer, in the same manner as for Southern blotting analysis, and detection was conducted also in the same manner.

(7) Sequence Analysis

Analysis of a sequence of base was conducted using Big Dye Terminator v3.0 Ready Reaction Cycle sequencing Kit (manufactured by Applied Biosystems). Using QIAEX II Gel Extraction Kit (manufactured by QIAGEN) as a template, a sequence reaction solution was produced containing cDNA fragments recovered from gel (cDNA fragment: template concentration, 100 to 200 bp: 2 ng/μl, 200 to 500 bp: 5 ng/μl, 500 to 1000 bp: 10 ng/μl, 1000 to 2000 bp: 20 ng/μl, >2000 bp: 50 ng/μl), 1×Terminator Ready Reaction PreMix, 1×sequencing buffer [80 mM Tris-HCl (pH 9.0), 2 mM $MgCl_2$, 0.01% BSA] and 1 pmol/μl primer, and incubation at 95° C. for 30 seconds was conducted once, then, a reaction cycle at 95° C. for 30 seconds and at 60° C. for 4 minutes was repeated 30 times, to effect a sequence reaction. This reaction solution was subjected to purification of the reaction product using a spin column prepared by filling Multiscreen HV plate (manufactured by MILLIPORE) with Sephadex G-50 fine (manufactured by Amarsham Pharmacia), and the purified substance was dried to solid in an oven at 65° C. This was dissolved completely with 30 μl of Template suspension reagent, and heated at 95° C. for 10 minutes for thermal denaturation, then, rapidly chilled taking 10 minutes with ice water, and the produced was analyzed using ABI PRISM 310 Genetic Analyzer.

Sequences of base of genes of thus obtained mutants M24, M5 and J18 are given by the sequence Nos. 3, 4 and 5 of the sequence listing.

Next, for producing a soybean oil of a decreased content of polyunsaturated fatty acids according to the present invention, soybean mutant strains obtained as described above are hybridized, selected and raised, to cause proliferation and cultivation, obtaining seeds. In this operation, it is optional that the mutant contains a single kind of gene or contains two or more kinds of genes.

In the cases of soybean mutants KK21 and M23, a microsomal ω-6 fatty acid desaturase enzyme producing linolic acid from oleic acid is deficient, therefore, production of linolic acid and, linolenic acid obtained by further change of linolic acid is suppressed, obtaining a soybean oil of a decreased content of linolic acid and linolenic acid, and in the cases of soybean mutants M24, M5 and J18, a microsomal ω-3 fatty acid desaturase enzyme producing linolenic acid from linolic acid is deficient, therefore, a soybean oil of a decreased content of linolenic acid is obtained.

What is claimed is:

1. A method for detecting a mutant gene from soybean mutant strain M23, said method comprises:

performing a RT-PCR amplification reaction on a part of the base sequence of the cDNA of gene GmFAD2-1 obtained from a soybean plant using primer 1: 5'-atgatagcccctccgttcccaaga-3' (SEQ ID NO: 6) and primer 4: 5'-atacacacaaagtcat&acgcggcaa-3' (SEQ ID NO: 9); and analyzing the RT-PCR reaction product by electrophoresis, wherein the absence of a 1.3 kilobase band is indicative of the presence of the mutant gene.

* * * * *

SEQUENCE LISTING

<160> NUMBER OF SEQ ID NOS: 5

<210> SEQ ID NO 1
<211> LENGTH: 1356
<212> TYPE: DNA
<213> ORGANISM: soybean (Glycine max)

<400> SEQUENCE: 1

```
tatttgcatt gtattgatag cccctccatt cccaagagta taaaactgca tcgaataata      60
caagccacta ggcatgggtc tagcaaagga aacaacaatg ggaggtagag gtcgtgtggc     120
caaagtggaa gttcaaggga agaagcctct ctcaagggtt ccaaacacaa agccaccatt     180
cactgttggc caactcaaga aagcaattcc accacactgc tttcagcgct ccctcctcac     240
ttcattctcc tatgttgttt atgacctttc atttgccttc attttctaca ttgccaccac     300
ctactccacc tccttcctca acccttttcc ctcattgcat ggccaatcta ttgggttctc     360
caaggttgcc ttctcactgg tgtgtgggtg attgctcacg agtgtggtca ccatgccttc     420
agcaagtacc aatgggttga tgatgttgtg ggtttgaccc ttcactcaac acttttagtc     480
ccttatttct catggaaaat aagccatcgc cgccatcact ccaacacagg ttcccttgac     540
cgtgatgaag tgtttgtccc aaaaccaaaa tccaaagttg catggttttc caagtactta     600
aacaaccctc taggaagggc tgtttctctt ctcgtcacac tcacaatagg gtggcctatg     660
tatttagcct tcaatgtctc tggtagaccc tatgatagtt ttgcaagcca ctaccaccct     720
tatgctccca tatattctaa ccgtgagagg cttctgatct atgtctctga tgttgctttg     780
ttttctgtga cttactctct ctaccgtgtt gcaaccctga aagggttggt ttggctgcta     840
tgtgtttatg gggtgccttt gctcattgtg aacggttttc ttgtgactat cacatatttg     900
cagcacacac actttgcctt gcctcattac gattcatcag aatgggactg gctgaaggga     960
gctttggcaa ctatggacag agattatggg attctgaaca aggtgtttca tcacataact    1020
gatactcatg tggctcacca tctcttctct acaatgccac attaccatgc aatggaggca    1080
accaatgcaa tcaagccaat attgggtgag tactaccaat ttgatgacac accatttac    1140
aaggcactgt ggagagaagc gagagagtgc ctctatgtgg agccagatga aggaacatcc    1200
gagaagggcg tgtattggta caggaacaag tattgatgga gcaaccaatg ggccatagtg    1260
ggagttatgg aagttttgtc atgtattagt acataattag tagaatgtta taaataagtg    1320
gatttgccgc gtaatgactt tgtgtgtatt gtgaaa                              1356
```

<210> SEQ ID NO 2
<211> LENGTH: 1357
<212> TYPE: DNA
<213> ORGANISM: soybean (Glycine max)

<400> SEQUENCE: 2

```
tatttgcatt gtattgatag cccctccatt cccaagagta taaaactgca tcgaataata      60
caagccacta ggcatgggtc tagcaaagga aacaacaatg ggaggtagag gtcgtgtggc     120
caaagtggaa gttcaaggga agaagcctct ctcaagggtt ccaaacacaa agccaccatt     180
cactgttggc caactcaaga aagcaattcc accacactgc tttcagcgct ccctcctcac     240
ttcattctcc tatgttgttt atgacctttc atttgccttc attttctaca ttgccaccac     300
ctacttccac ctccttcctc aaccctttcc cctcattgca tggccaatct attgggttct     360
ccaaggttgc cttctcactg gtgtgtgggt gattgctcac gagtgtggtc accatgcctt     420
```

```
cagcaagtac caatgggttg atgatgttgt gggtttgacc cttcactcaa cacttttagt      480
cccttatttc tcatggaaaa taagccatcg ccgccatcac tccaacacag gttcccttga      540
ccgtgatgaa gtgtttgtcc caaaaccaaa atccaaagtt gcatggtttt ccaagtactt      600
aaacaaccct ctaggaaggg ctgtttctct tctcgtcaca ctcacaatag ggtggcctat      660
gtatttagcc ttcaatgtct ctggtagacc ctatgatagt tttgcaagcc actaccaccc      720
ttatgctccc atatattcta accgtgagag gcttctgatc tatgtctctg atgttgctttt     780
gttttctgtg acttactctc tctaccgtgt tgcaaccctg aaagggttgg tttggctgct      840
atgtgtttat ggggtgcctt tgctcattgt gaacggtttt cttgtgacta tcacatattt      900
gcagcacaca cactttgcct tgcctcatta cgattcatca gaatgggact ggctgaaggg      960
agctttggca actatggaca gagattatgg gattctgaac aaggtgtttc atcacataac     1020
tgatactcat gtggctcacc atctcttctc tacaatgcca cattaccatg caatggaggc     1080
aaccaatgca atcaagccaa tattgggtga gtactaccaa tttgatgaca caccatttta     1140
caaggcactg tggagagaag cgagagagtg cctctatgtg gagccagatg aaggaacatc     1200
cgagaagggc gtgtattggt acaggaacaa gtattgatga agcaaccaat gggccatagt     1260
gggagttatg gaagttttgt catgtattag tacataatta gtagaatgtt ataaataagt     1320
ggatttgccg cgtaatgact ttgtgtgtat tgtgaaa                              1357

<210> SEQ ID NO 3
<211> LENGTH: 1405
<212> TYPE: DNA
<213> ORGANISM: soybean (Glycine max)

<400> SEQUENCE: 3
tcttctaggt tattacgcac cacccaccac gtatccctga aaagagagaa aaacacacta      60
agccaaagcc aaagcagcaa tggttaaaga cacaaagcct ttagcctatg ctgccaataa      120
tggataccaa caaagggtt cttcttttga ttttgatcct agcgctcctc caccgtttaa      180
gattgcagaa atcagagctt caataccaaa acattgctgg gtcaagaatc catggagatc      240
cctcagttat gttctcaggg atgtgcttgt aattgctgca ttggtggctg cagcaattca      300
cttcgacaac tggcttctct ggctaatcta ttgccccatt caaggcacaa tgttctgggc      360
tctcttttgtt cttggacatg attgtggcca tggaagcttt tcagatagcc ctttgctgaa      420
tagcctggtg ggacacatct tgcattcctc aattcttgtg ccataccatg gatggagaat      480
tagccacaga actcaccatc aaaaccatgg acacattgag aaggatgagt catgggttcc      540
attaacagag aagatttaca agaatctaga cagcatgaca agactcatta gattcactgt      600
gccatttcca ttgtttgtgt atccaattta tttgttttca agaagccccg aaaggaagg      660
ctctcacttc aatccctaca gcaatctgtt cccacccagt gagagaaaag gaatagcaat      720
atcaacactg tgttgggcta ccatgttttc tctgcttatc tatctctcat tcataactag      780
tccacttcta gtgctcaagc tctatggaat tccatattgg atatttgtta tgtggctgga      840
cttttgtcaca tacttgcatc accatggtca ccaccagaaa ctgccttggt accgcggcaa      900
ggaatggagt tatttaagag gtggcctcac cactgtggat cgtgactatg gttggatcta      960
taacattcac catgacattg gcacccatgt tatccaccat cttttccccc aaattcctca     1020
ttatcacctc gttgaagcga cacaagcagc aaaaccagtt cttggagatt actaccgtga     1080
gccagaaaga tctgcgccat taccatttca tctaataaag tatttaattc agagtatgag     1140
```

-continued

```
acaagaccac ttcgtagtga cactggagat gttgtttatt atcagactga ttctctgctc        1200
ctccactcgc aacgagactg agtttcaaac ttttggggtt attatttatt ggattctagc        1260
tactcaaatt acttttttt taatgttatg ttttttggag tttaacgttt tctgaacaac         1320
ttgcaaatta cttgcataga gagacatgga atatttattt gaaattagta aggtagtaat       1380 aataaattt gaattgtcag tttca                                              1405
```

<210> SEQ ID NO 4
<211> LENGTH: 1376
<212> TYPE: DNA
<213> ORGANISM: soybean (Glycine max)

<400> SEQUENCE: 4

```
tcttctaggt tattacgcac cacccaccac gtatccctga aaagagagaa aaacacacta         60
agccaaagcc aaagcagcaa tggttaaaga cacaaagcct ttagcctatg ctgctaataa        120
tggataccaa caaggaagct tttgatccca gtgctcctcc accgtttaag attgcagaaa       180
tcagagttgc aataccaaaa cattgctggg tcaagaatcc atggagatcc ctcagttatg       240
ttctcaggga tgtgcttgta attgctgcat tgatggctgc tgcaagtcac ttccacaact       300
ggcttctctg ctaatctat tggcccattc aaggaacaat gttctgggct ctgtttgttc        360
ttggacatga ttgtggccat ggaagctttt cagacagccc ttttctaaat agcctggtgg      420
gacacatctt gcattcctca attcttgtgc ataccatgg atggagaatt agccacagaa        480
ctcaccatca aaatcatgga cacattgaga aggatgaatc ctgggttcca ttaaccgaga       540 agattacaa gaatctagac aacatgacaa gacttgttag attcactgtg ccatttccat        600
tgtttgtgta tccaatttat ttgttctcaa gaagccccgg aaaggaaggt tctcacttca       660
atccctacag caatctgttc ccacccagtg agagaaaggg aatagcaata tcaacactgt       720
gttgggttac catgttttct atgcttatct atctctcctt cataactagt ccagttctat       780
tgctcaagct ctatggaatt ccatattgga tatttgttat gtggctggac tttgtcacat       840
acttgcatca ccatggtcat catcagaaac tgccttggta tcgcggcaag gaatggagtt       900
atttaagagg tggtctcaca actgtggatc gtgactatgg ttggatcaat aacattcacc       960
atgacattgg cacccatgtt atccatcatc ttttccctca aattcctcat tatcacctcg      1020
ttgaagcgac acaagcagca aaatcagttc ttggagagta ttaccgtgag ccagaaagat      1080
ctgcgccatt accatttcat ctaataaagt atttaattca gagtatgaga caagaccaga      1140
tgtggtttat tatcagactg attctctgct cctccactcg caacgagact gagtttcaaa      1200
ctttttgggt tattatttat tggattctag ctactcaaat tactttttttt ttaatgttat      1260 gtttttttgga gtttaacgtt ttctgaacaa cttgcaaatt acttgcatag agagacatgg      1320
aatatttatt tgaaattagt aaggtagtaa taataaattt gaattgtca gtttca           1376
```

<210> SEQ ID NO 5
<211> LENGTH: 1395
<212> TYPE: DNA
<213> ORGANISM: soybean (Glycine max)

<400> SEQUENCE: 5

```
tcttctaggt tattacgcac cacccaccac gtatccctga aaagagagaa aaacacacta         60
agccaaagcc aaagcagcaa tggttaaaga cacaaagcct ttagcctatg ctgctaataa        120
tggataccaa caaggaagct tttgatccca gtgctcctcc accgtttaag attgcagaaa       180
tcagagttgc aataccaaaa cattgctggg tcaagaatcc atggagatcc ctcagttatg       240
```

```
ttctcaggga tgtgcttgta attgctgcat tgatggctgc tgcaagtcac ttccacaact    300
ggcttctctg gctaatctat tggcccattc aaggaacaat gttctgggct ctgtttgttc    360
ttggacatga ttgtggccat ggaagctttt cagacagccc ttttctaaat agcctggtgg    420
gacacatctt gcattcctca attcttgtgc cataccatgg atggagaatt agccacagaa    480
ctcaccatca aaatcatgga cacattgaga aggatgaatc ctgggttcca ttaaccgaga    540
agatttacaa gaatctagac aacatgacaa gacttgttag attcactgtg ccatttccat    600
tgtttgtgta tccaatttat ttgttctcaa gaagccccgg aaaggaaggt tctcacttca    660
atccctacag caatctgttc ccacccagtg agagaaaggg aatagcaata tcaacactgt    720
gttgggttac catgttttct atgcttatct atctctcctt cataactagt ccagttctat    780
tgctcaagct ctatggaatt ccatattgga tatttgttat gtggctggac tttgtcacat    840
acttgcatca ccatggtcat catcagaaac tgccttggta tcgcggcaag gaatggagtt    900
atttaagagg tggtctcaca actgtggatc gtgactatgg ttggatcaat aacattcacc    960
atgacattgg cacccatgtt atccatcatc ttttccctca aattcctcat tatcacctcg   1020
ttgaagcgac acaagcagca aaatcagttc ttggagagta ttaccgtgag ccagaaagat   1080
ctgcgccatt accatttcat ctaataaagt atttaattca gagtatgaga caagaccact   1140
tcgtaagtga cactggagat gtggtttatt atcagactga ttctctgctc ctccactcgc   1200
aacgagactg agtttcaaac ttttgggtt attatttatt ggattctagc tactcaaatt   1260
acttttttt taatgttatg tttttggag tttaacgttt tctgaacaac ttgcaaatta   1320
cttgcataga gagacatgga atatttattt gaaattagta aggtagtaat aataaatttt   1380
gaattgtcag tttca                                                    1395
```